United States Patent
Oberlaender et al.

(10) Patent No.: US 8,066,630 B2
(45) Date of Patent: Nov. 29, 2011

(54) HOLDING AND RESTING DEVICE FOR MEDICAL INSTRUMENTS HAVING ESSENTIALLY CYLINDRICAL INSTRUMENTAL BODIES

(75) Inventors: Martin Oberlaender, Engen (DE); Michael Sauer, Tuttlingen (DE); Jochen Schmidberger, Schoemberg (DE)

(73) Assignee: Karl Storz GmbH & Co. KG (DE)

(*) Notice: Subject to any disclaimer, the term of this patent is extended or adjusted under 35 U.S.C. 154(b) by 1034 days.

(21) Appl. No.: 11/224,453

(22) Filed: Sep. 12, 2005

(65) Prior Publication Data
US 2006/0058579 A1  Mar. 16, 2006

(30) Foreign Application Priority Data
Sep. 11, 2004  (DE) .................. 10 2004 043 982

(51) Int. Cl.
A61B 1/00  (2006.01)
A61M 5/178  (2006.01)
(52) U.S. Cl. .............. 600/102; 604/167.06; 600/154
(58) Field of Classification Search .......... 600/102, 600/121, 125, 101, 104, 106, 154; 604/164.07, 604/165.01–165.04, 167.06, 178, 533–536
See application file for complete search history.

(56) References Cited

U.S. PATENT DOCUMENTS

| 4,287,891 | A | | 9/1981 | Peters ........................ 128/34 |
| 5,263,939 | A | | 11/1993 | Wortrich ..................... 604/174 |
| 5,275,614 | A | | 1/1994 | Haber et al. ................ 606/207 |
| 5,366,446 | A | | 11/1994 | Tal et al. ..................... 604/110 |
| 5,380,302 | A | * | 1/1995 | Orth ............................ 604/523 |
| 5,441,042 | A | | 8/1995 | Putman |
| 5,505,714 | A | * | 4/1996 | Dassa et al. ................ 604/534 |
| 5,803,079 | A | * | 9/1998 | Rogers et al. ........... 128/207.14 |
| 5,944,696 | A | | 8/1999 | Bayless et al. |
| 6,190,372 | B1 | * | 2/2001 | Racz ........................... 604/534 |
| 6,228,059 | B1 | | 5/2001 | Astarita ................. 604/164.07 |
| 6,428,514 | B1 | | 8/2002 | Goebel et al. |

FOREIGN PATENT DOCUMENTS

| DE | 196 25 729 | | 1/1998 |
| DE | 202 14 608 | | 1/2003 |
| EP | 0 367 549 | | 5/1990 |
| EP | 0 426 407 | | 5/1991 |
| EP | 0 648 470 | | 4/1995 |
| NL | 1015663 | C2 | 1/2002 |
| WO | 90/11454 | | 10/1990 |

OTHER PUBLICATIONS

European Office Action Dated Mar. 11, 2008, 4 pages. European Search Report; Dec. 5, 2005; 5 pages.
Record of Oral Hearing at the German Patent Office; Application No. 10 2004 043 986.6; Sep. 14, 2009; 2 pages.

* cited by examiner

Primary Examiner — Matthew J Kasztejna
Assistant Examiner — Ryan Henderson
(74) Attorney, Agent, or Firm — St. Onge Steward Johnston & Reens LLC

(57) ABSTRACT

The invention relates to a holding and resting device for medical instruments having essentially cylindrical instrument bodies, in particular endoscopic instruments, with a base body that can be secured for instance to an operating table and an instrument input to be inserted into the base body and in which the instrument body can be secured by clamping. To create a holding and resting device for medical instruments having essentially cylindrical instrument bodies, which is of simple construction and can be activated quickly and safely, it is proposed with the invention that the instrument input includes a ring-shaped tension casing with at least two holder arms as well as a tension nut that works together with the tension casing.

3 Claims, 2 Drawing Sheets

HOLDING AND RESTING DEVICE FOR MEDICAL INSTRUMENTS HAVING ESSENTIALLY CYLINDRICAL INSTRUMENTAL BODIES

This application claims priority of German Patent Application No. 10 2004 043 982.6 filed on Sep. 11, 2004.

FIELD OF THE INVENTION

The invention relates to a holding and resting device for medical instruments having essentially cylindrical instrumental bodies, in particular endoscopic instruments, with a base body that can be secured for instance on an operating table and an instrument input that can be inserted into the base body and into which the instrument body can be secured by clamping.

BACKGROUND OF THE INVENTION

Holding and resting devices of this type are, for instance, positioned on operating tables to allow the operator during the operation to safely lie down and pick up instruments again, for instance a laparoscope or endoscope, without requiring operating personnel for the task. It is important in such holding devices that they secure the medical instrument that is to be inserted, securely and as immovably as possible, especially to prevent the instruments from falling down.

A holding and resting device familiar from practical use includes for this purpose an instrument input, in which the instrument body of the medical instrument that is to be held can be secured by clamping, and the clamped holding is effected by a tension screw that, after several rotations, narrows the instrument input in such a way that the instrument body is securely held. This known holding and resting device ensures a secure fixing of the medical instrument to be inserted, but it is complicated for the operator to manipulate, because releasing the tension screw takes time first of all and secondly can be performed in most cases only by both hands.

SUMMARY OF THE INVENTION

Consequently it is the object of this invention to provide a holding and resting for medical instruments that has an essentially cylindrical instrument body and is simple in construction and safe to operate.

This object is fulfilled by the invention in that the instrument intake has a ring-shaped tension casing with at least two holding arms and a tension nut that works together with the tension casing.

The inventive equipment of the instrument input with the tension casing as well as the nut that works with the tension casing permits a simple, cost-effective structure of the holding and resting device.

According to a practical embodiment of the invention it is proposed that the holder arms of the tension casing can be reshaped essentially radially by means of tension elements configured on the tension nut. The instrument body is held by clamping in the instrument intake by the radially inward reshaping of the holder arms of the tension pincers if the tension elements of the tension nut are in contact with the holder arms. Because the holder arms of the tension pincers are pressed inward by clamping by every tension element, these cooperating tension tools form a speed tension lock so that it requires no complete rotation of the tension nut to securely fix a medical instrument inserted into the holding device and to release it again.

The inventive tension casing advantageously includes four holder arms arranged around the circumference of the ring-shaped tension casing which can be reshaped by means of four cogs configured on the tension nut and serving as tension elements. With this embodiment it requires only one-fourth of a rotation of the tension nut in order to move the holding device from the open position into the clamping position or from the clamping position into the open position.

It is further proposed with the invention that a ring-shaped holder element consisting of an elastically reshapable material for inserting the instrument body can be inserted into the tension casing. This holder element improves a secure and protective holding of the instrument body in the instrument input.

In order, first, to facilitate inserting the instrument body into the elastically reshapable holder element of the instrument insert and, second, to avoid the occurrence of so-called grating sound because of the stick-slip effect, the inner surface of the elastic holder element facing the instrument body that is to be inserted is adjacent to the instrument body only in some areas in the clamping position. Because the stick-slip effect occurs because of a reciprocal effect of the locking and sliding friction of two materials sliding along one another, the minimization of the mutual contact surfaces constitutes an appropriate means of avoiding this grating sound.

It is finally proposed with a preferred embodiment of the invention that to minimize the contact surfaces, the inner surface of the elastic holder element facing the instrument body that is to be inserted should be configured as toothed.

Additional characteristics and advantages of the invention can be seen from the related illustration, in which an embodiment of an inventive holding and resting device for medical instruments having essentially cylindrical instrument bodies is depicted only in exemplary fashion.

DETAILED DESCRIPTION OF THE DRAWINGS

Figure 1:
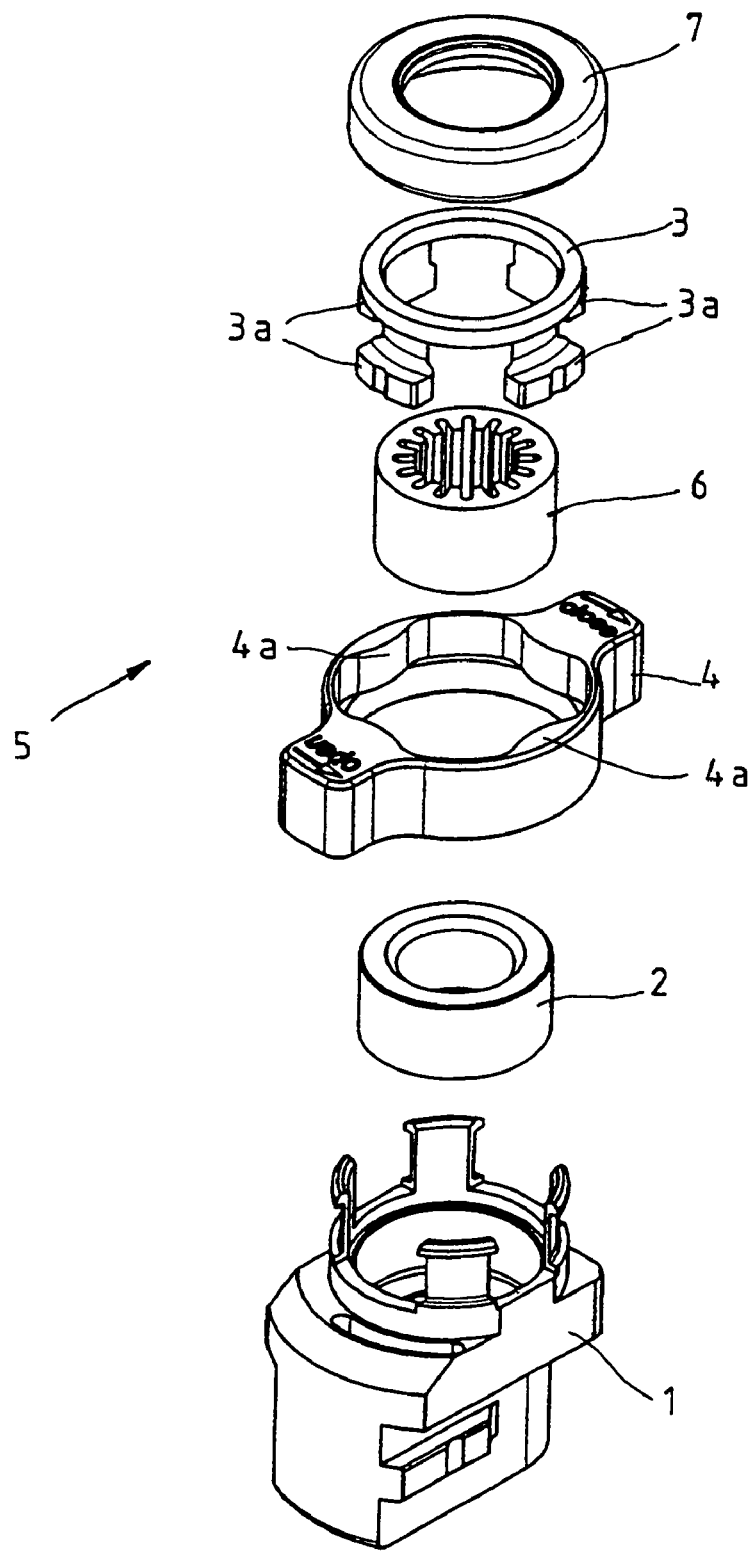
FIG. 1 shows an explosion drawing of an inventive holding and resting device for medical instrument with an instrument body that is essentially cylindrical.
Figure 2:
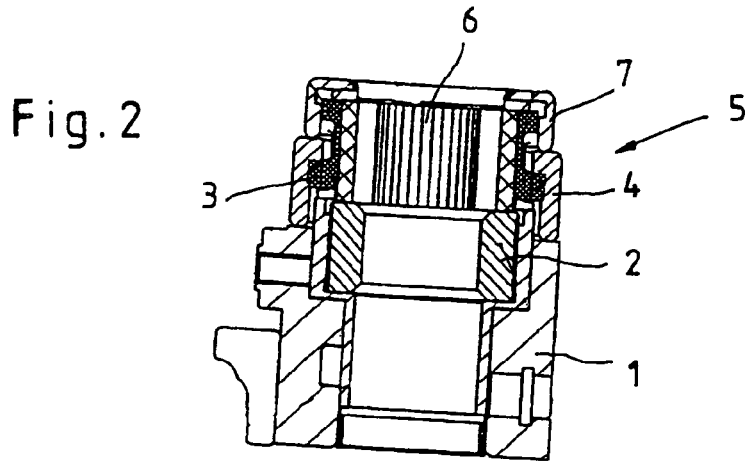
FIG. 2 shows a longitudinal section through the holding device shown in FIG. 1 in assembled condition.

The holding and resting device depicted in the illustrations for medical instruments having essentially cylindrical instrument bodies consists, as can be seen in particular from the explosion view in FIG. 1, of a base body 1 that can be secured, for instance, on an operating table as well as a guide ring 2 that can be inserted into the base body 1, a ring-shaped tension casing 3 that includes four holder arms 3a, and a tension nut 4 that can be mounted on the tension casing 3, which together form an instrument input 5, as well as a ring-shaped holder element 6 that can be inserted into the tension casing 3 of the instrument input 5 and an upper covering ring 7.

As an alternative to securing the base body 1 of the holding and resting device on an operating table, it is of course also possible to secure the base body 1 on a different object, for instance an instrument table or a separate stand.

Figure 3:
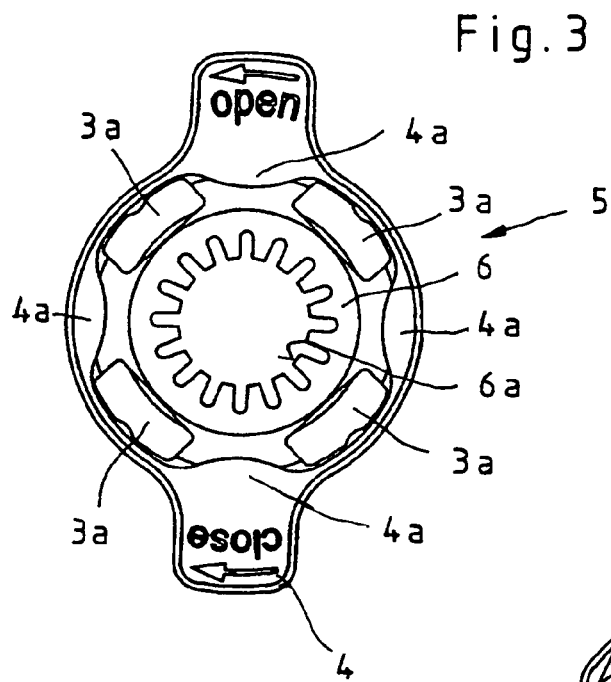
FIG. 3 shows a partial overhead view of the holding device of FIG. 2, depicting the open position.
Figure 4:
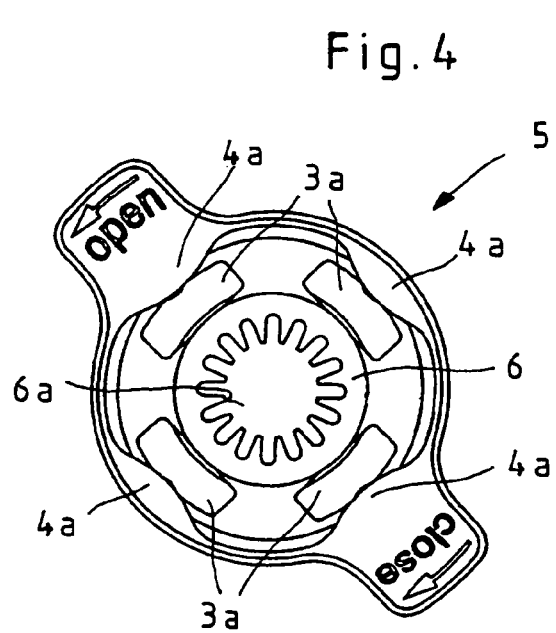
FIG. 4 shows an overhead view according to FIG. 3, but showing the clamping position.

FIGS. 1, 3, and 4 in particular indicate the structure and mode of operation of the instrument input 5 consisting of the tension casing 3 and the tension nut 4 and which serves for inserting and fixing the instrument body of a medical instrument inserted into the holding device, for instance a laparoscope or endoscope.

As can be seen in particular from the overhead views in FIGS. 3 and 4, the tension nut 4 on its inner side facing the tension casing 3 includes four tension elements configured as cogs 4a which cause the clamping cooperation of the tension casing 3 and the tension nut 4.

A medical instrument inserted into the instrument input 5 is grasped by clamping as follows:

In the open position of the instrument input 5 shown in FIG. 3 the cogs 4a of the tension nut 4 coaxially surrounding the tension casing 3 are positioned alternating in each case between the holder arms 3a of the tension casing 3. As soon as the tension nut 4 is rotated by a quarter-turn to right or left, the cogs 4a of the tension nut 4 come in contact with the holder arms 3a of the tension casing 3 and press them essentially radially inward, so that the input area in the interior of the tension casing is reduced in diameter, as this is shown by the clamping position illustrated in FIG. 4.

An instrument body positioned in this input area is gripped in the clamping position by the radially inward reshaped holder arms 3a of the tension casing 3 by clamping and secured in its position.

To open the instrument input 5, it is necessary only to rotate the tension nut 4 again by a quarter-turn to right or left until the cogs 4a of the tension nut 4 are no longer engaged with the holder arms 3a of the tension casing 3.

In the illustrated embodiment of a holding device, even when preferred turning instructions are given for opening and closing the instrument input 5, the theoretical possibility exists of turning the tension nut 4 to open and close the instrument input 5 in both directions each time, because of the structural configuration.

Likewise it is of course possible to equip the tension casing 3 with a fewer or more holder arms 3a. To ensure simple and rapid activation of the instrument input 5, it is advantageous if the number of cogs 4a of the tension nut 4 corresponds to the number of holder arms 3a of the tension casing 3.

As can also be seen from the illustrations, the instrument input 4 still has a ring-shaped holder element 6 inserted in the tension casing 3, which element is made of an elastic material and serves to ensure a safe and protective holding of the instrument body inserted into the instrument input 5. Contrary to the holder arms 3a radially arched inward and only gripping at certain points, the holder element 6 embraces the entire input space and thus also the entire instrument body.

To facilitate insertion of the instrument body into the elastically reshapable holder element 6, which preferably consists of a rubber type of material, and to avoid the occurrence of so-called grating noise from the stick-slip effect, the inner surface 6a of the elastic holder element 6 facing the instrument body that is to be inserted is adjacent in the clamping position only in some areas to the instrument body. In the illustrated embodiment the inner surface 6a of the holder element 6 is configured as toothed for this purpose.

With the stick-slip effect—also known as backsliding—two materials stimulated by relative movement to one another come into a reciprocal action between grasping and sliding friction. This back-and-forth between sliding and interlocking is the cause of this grating sound. By minimizing the contact surfaces between the holder element 6 on the one hand and the instrument body on the other, the occurrence of the stick-slip effect on inserting and removing the instrument body from the instrument input 5 is avoided.

A holding and resting device configured as described, for medical instruments having essentially cylindrical instrument bodies is distinguished in that the instrument input 5 is configured as a quick tension lock. This design allows the operator simple and secure operation of the holding device, even when only one hand is used.

What is claimed is:

1. A holding and resting device for medical instruments having cylindrical instrument bodies comprising a base body secured to an operating table and an instrument receptacle that is inserted into the base body and in which the instrument body is secured by clamping, distinguished in that the instrument receptacle comprises a ring-shaped clamping sleeve which includes at least two holder arms and further comprises a tightening nut working together with the clamping sleeve, wherein the instrument body is released and secured in the instrument receptacle by said tightening nut and in that a ring-shaped holder element comprises an elastically reshapable material that is inserted into the clamping sleeve for receiving the instrument body, wherein an inner surface of the elastic holder element facing the inserted instrument body is configured as toothed even in an unclamped position with each tooth being in linear contact with the instrument body with respect to the direction of insertion in the unclamped position and is in contact with the instrument body in the clamping position only in some areas, and wherein not more than one half of the total inner surface of the elastic holder element is in contact with the instrument body when in the unclamped and clamped positions.

2. A holding and resting device according to claim 1, distinguished in that the holder arms of the clamping sleeve can be re-shaped radially by using clamping elements configured on the tightening nut.

3. A holding and resting device according to claim 2, distinguished in that the clamping sleeve has four holder arms uniformly positioned around the circumference of the ring-shaped clamping sleeve, which can be reshaped by four cogs configured on the tightening nut that serve as clamping elements.

* * * * *